(12) United States Patent
Sharoni et al.

(10) Patent No.: US 11,758,863 B2
(45) Date of Patent: Sep. 19, 2023

(54) *PORTULACA* VARIETY NAMED 'DAPORUMDBL'

(71) Applicant: Danziger DAN' Flower Farm, Beit Dagan (IL)

(72) Inventors: Pazit Sharoni, Beit Dagan (IL); Amir Zuker, Beit Dagan (IL); Gavriel Danziger, Beit Dagan (IS)

(73) Assignee: Danziger "DAN" Flower Farm

( * ) Notice: Subject to any disclaimer, the term of this patent is extended or adjusted under 35 U.S.C. 154(b) by 23 days.

(21) Appl. No.: 17/495,624

(22) Filed: Oct. 6, 2021

(65) Prior Publication Data

US 2023/0108151 A1  Apr. 6, 2023

(51) Int. Cl.
*A01H 6/30* (2018.01)
*A01H 5/10* (2018.01)
*A01H 5/02* (2018.01)

(52) U.S. Cl.
CPC ............ *A01H 6/30* (2018.05); *A01H 5/02* (2013.01); *A01H 5/10* (2013.01)

(58) Field of Classification Search
CPC ... A01H 6/00; A01H 6/30; A01H 5/10; A01H 5/02
USPC .......................................................... Plt./471
See application file for complete search history.

(56) References Cited

U.S. PATENT DOCUMENTS

2020/0367416 P1 * 11/2020 Danziger ............. A01H 6/00
Plt./471

OTHER PUBLICATIONS

McFarling (Huntington Frontiers, A Garden in Deep Freeze, posted May 12, 2016 and downloaded from huntington.org/frontiers/garden-deep-freeze.*
Walter R. Fehr, Principles of Cultivar Development, vol. 1 Theory and Technique, 1987, pp. 28-29.*

* cited by examiner

*Primary Examiner* — Susan McCormick Ewoldt
(74) *Attorney, Agent, or Firm* — Cassandra Bright

(57) ABSTRACT

The invention relates to the field of *Portulaca umbracticola*, specifically, the variety designated 'DAPORUMDBL'. The variety 'DAPORUMDBL' is characterized by its unique full flowers with extra petals in the flower center. Plants exhibit low fertility with very low seed production and scant pollen. The present invention relates to plant parts, including cells and any propagative material of the new variety 'DAPORUMDBL', and use of any of the plant parts for reproducing the new variety 'DAPORUMDBL'. The present invention relates to methods using any plant parts of 'DAPORUMDBL' for the purpose of deriving additional new *Portulaca* varieties. The present invention relates to seed, plants and plant parts produced by crossing 'DAPORUMDBL' with any other *Portulaca* variety or other plant. The present invention also relates to methods to produce new varieties of *Portulaca umbracticola* and ornamental plants using the variety 'DAPORUMDBL' and applying plant breeding techniques.

9 Claims, 2 Drawing Sheets
(2 of 2 Drawing Sheet(s) Filed in Color)

PORTULACA VARIETY NAMED 'DAPORUMDBL'

FIELD AND BACKGROUND OF THE INVENTION

The present invention relates to a new variety of *Portulaca umbraticola* referred to as 'DAPORUMDBL' as well as to new, distinct and stable characteristics found in *Portulaca umbraticola*. The present invention relates to plants which have all of the morphological and physiological characteristics described herein, as well as plant parts which can be used to reproduce plants having the characteristics specific to *Portulaca umbraticola* referred to as 'DAPORUMDBL'. The present invention also relates to methods for producing these plants of *Portulaca umbraticola* exhibiting the characteristics described herein. Furthermore, the present invention relates to a method of producing progeny *Portulaca* plants by crossing the *Portulaca umbraticola* referred to as 'DAPORUMDBL', as either the female or seed or male or pollen parent, with another *Portulaca* plant and selecting progeny. The present invention also relates to methods to produce new varieties of *Portulaca umbraticola* using the variety 'DAPORUMDBL' in a breeding program.

*Portulaca* is a member of the *Portulacaceae* family. *Portulaca umbraticola* is a vascular land plant, with a nearly worldwide distribution. *Portulaca umbraticola* is a succulent annual, widely used in the ornamental horticultural sector. Flowers are vibrantly colored and plants well suited for container and garden uses. This makes *Portulaca umbraticola* an important target for the breeding of new varieties with novel characteristics. There is a demand for new varieties of *Portulaca*.

Asexual propagation of *Portulaca* can be performed by vegetative basal cuttings, however, propagation can also be performed by sowing seeds.

The new *Portulaca* cultivar is a product of a planned breeding program conducted by the inventors, Pazit Sharoni, Amir Zuker and Gavriel Danziger, in Moshav Mishmar Hashiva, Israel. The objective of the breeding program was to produce useful new *Portulaca* varieties for ornamental horticultural production. The open-pollination resulting in this new variety was made during the Summer of 2014.

A need exists for a greater variety of *Portulaca* cultivars with vigorous yet controlled plant habits. Larger flowers are also a desirable feature for the ornamental horticulture market.

A new *Portulaca umbraticola* variety has been developed through a controlled breeding program and exhibits unique, desirable and stable characteristics. The *Portulaca* variety illustrated herein is referred to as 'DAPORUMDBL'.

The parent is the unpatented, propriety variety referred to as *Portulaca* 'PT-13-1115'. The new *Portulaca* 'DAPORUMDBL' originated from the process of self-pollination of the parent variety. The parental cultivar has a sufficient degree of homozygosity such that the progeny of the cross are genotypically and phenotypically uniform. The new variety was discovered in July of 2017 by the inventor in a group of seedlings resulting from the 2016 self-pollination, in a greenhouse in Moshav Mishmar Hashiva, Israel. After selection of the new variety, extensive confidential testing has been performed to determine and define the desirable characteristics of the new variety.

The new variety 'DAPORUMDBL' can be produced by asexual reproduction to produce a population of progeny plants, each of which has the combination or characteristics as herein disclosed for the new variety.

Deposit Information

Seeds which can be used to produce the variety 'DAPORUMDBL' have been deposited with the National Collection of Industrial Food and Marine Bacteria(NCIMB), Ferguson Building, Bucksburn, Aberdeen, Scotland, a Budapest Treaty recognized depository which affords permanence of the deposit. Accession Number NCIMB 43738 has been assigned to this deposit. This deposit has been accepted under the Budapest Treaty.

Objects of the Invention

The following embodiments and aspects thereof are described in conjunction with system, tools and methods which are meant to be exemplary, not limiting in scope The present invention, in some embodiments thereof, relates to *Portulaca umbraticola* plants and characteristics of these plants.

*Portulaca umbraticola*, also known as 'Purslane', is valued as an ornamental flowering annual. Due to its ornamental value, attempts have been made to generate varieties of *Portulaca umbraticola* incorporating novel and improved traits to the horticultural industry. Thus, whilst reducing the present invention to practice, the present inventors were able, to generate a unique variety of *Portulaca umbraticola*.

The present invention provides Portulaca plant selections with controlled, semi-trailing plant habits, with free-branching. Flowers are large and vivid dark pink, foliage is dark green. These characteristics in combination distinguish the new cultivar from typical *Portulaca umbraticola* varieties.

These and other objectives have been achieved in accordance with the present invention which are the product of a planned breeding program conducted by the inventors. One embodiment of this invention is the *Portulaca* variety 'DAPORUMDBL' described herein. The parent is the *Portulaca umbraticola* line identified by code 'PT-13-1115' (unpatented).

Seeds which can be used to produce the variety 'DAPORUMDBL' has been deposited with the National Collection of Industrial Food and Marine Bacteria(NCIMB), Ferguson Building, Bucksburn, Aberdeen, Scotland and assigned accession number NCIMB 43738.

Another embodiment relates to a plant produced from seeds which are *Portulaca umbraticola* 'DAPORUMDBL'.

Another embodiment relates to a plant produced by vegetative means which are *Portulaca umbraticola* 'DAPORUMDBL'. The present invention also relates to plant parts, such as pollen, seeds or inflorescence produced by *Portulaca umbraticola* 'DAPORUMDBL'.

Another embodiment relates to a method of producing seed which are *Portulaca umbraticola* 'DAPORUMDBL'.

Another embodiment also relates to a method of producing plants having all the physiological and morphological characteristics of the *Portulaca umbraticola* 'DAPORUMDBL'. comprising the steps of (a) self-pollinating *Portulaca umbraticola* 'DAPORUMDBL'. (b) harvesting seeds produced from said cross; and (c) producing plants from said harvested seeds.

The present invention also relates to producing progeny plants from the cross of *Portulaca umbraticola* 'DAPORUMDBL', as the female or male parent, with another *Portulaca* or other plant, and selecting progeny plants from this cross.

The present invention also relates to producing progeny plants of *Portulaca umbraticola* 'DAPORUMDBL', by any known means of vegetative propagation.

The present invention also relates to producing progeny plants of *Portulaca umbraticola* 'DAPORUMDBL', from natural or induced mutation.

Another embodiment relates to tissue culture produced from protoplast of cells from the *Portulaca* plant disclosed in the subject application, wherein said cells or protoplasts are produced from a plant part selected from the group consisting of pollen, ovules, embryos, protoplasts, meristematic cells, callus, leaves, anthers, cotyledons, hypcotyl, pistils, roots, root tips, flowers, seeds, petiole and stems.

Another embodiment relates to a plant or a part thereof, produced by growing *Portulaca umbraticola* 'DAPORUMDBL', wherein the plant part comprises at least one cell of *Portulaca umbraticola* 'DAPORUMDBL'.

Another embodiment relates to tissue or cell culture of regenerable cells produced from the plants of *Portulaca umbraticola* 'DAPORUMDBL'. This includes a *Portulaca umbraticola* plant regenerated from the tissue or cell culture of *Portulaca umbraticola* 'DAPORUMDBL'.

Another embodiment relates to a method of vegetatively propagating the plant *Portulaca umbraticola* 'DAPORUMDBL' comprising the steps of: collecting tissue or cells capable of being propagated from a plant of *Portulaca umbraticola* 'DAPORUMDBL'; cultivating said tissue or cells to obtain proliferated shoots; and rooted said shoots to obtain rooted plantlets; or cultivating said tissue or cells to obtain shoots or to obtain plantlets and a plant produced by growing the plantlets or shoots of said plant.

A further embodiment relates to a method for developing a *Portulaca umbraticola* plant in a *Portulaca* breeding program, comprising applying plant breeding techniques comprising crossing, 3 recurrent selection, mutation breeding, wherein said mutation breeding selects for a mutation that is 4 spontaneous or artificially induced, backcrossing, pedigree breeding, marker enhanced selection, 5 haploid/ double haploid production, or transformation to the *Portulaca* plant of *Portulaca umbraticola* 'DAPORUMDBL', or its parts, wherein application of said techniques results in development of an *Portulaca umbraticola* plant.

A further embodiment relates to a method of introducing a mutation into the genome of *Portulaca umbraticola* 'DAPORUMDBL', and wherein the resulting plant comprises at least one genome mutation and producing plants therefrom.

In addition to the exemplary aspects and embodiments described above, further aspects and 14 embodiments will become apparent by study of the following descriptions.

The cultivar 'DAPORUMDBL' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DAPORUMDBL' These characteristics in combination distinguish 'DAPORUMDBL' as a new and distinct Portulaca cultivar:
1. Full flower with extra petals in the flower center.
2. 4 or 5 stigma branches.
3. Low fertility with very low seed production.
4. Scant pollen production.

Parent Comparison

Plants of the new cultivar 'DAPORUMDBL' are similar to plants of the parent, in most horticultural characteristics, however, plants of the new cultivar 'DAPORUMDBL' differ in the following;

1. The new variety has a more controlled and rounded plant habit than the parent.
2. Foliage of the new variety is smaller than foliage of the parent.
3. The new variety flowers more abundantly than the parent.

Commercial Comparison

Plants of the new cultivar 'DAPORUMDBL' can be compared to the commercial variety *Portulaca* 'DPAZPINKGL', unpatented. 'These varieties are similar in most horticultural characteristics;
1. This comparator produces more seeds than 'DAPORUMDBL'.
2. The flowers of this comparator are single, without petals in the center; flowers of 'DAPORUMDBL' are double with extra petals in the center.
3. Plant habit of this comparator is less controlled than the plant habit of 'DAPORUMDBL'.
4. The new *portulaca* variety, has a variable number of stigma branches (4 or 5) while 'DPAZPINKGL' has 6 stigma branches.

BRIEF DESCRIPTION OF THE FIGURES

The patent or application file contains at least one drawing executed in color. Copies of this patent or patent application publication with color drawings will be provided by the Office upon request and payment of the necessary fees.

The accompanying photographs in FIGS. 1 and 2 illustrate the overall appearance of the new *Portulaca umbraticola* referred to as 'DAPORUMDBL'. Colors in the photographs may differ slightly from the color values cited in the detailed botanical description which accurately describes the color of 'DAPORUMDBL'.

Figure 1:
FIG. 1 illustrates in full color a typical plant of 'DAPORUMDBL' at about 10 weeks of age, grown in a 13 cm pot.
Figure 2:
FIG. 2 illustrates in full color a close-up view of typical flowers of the new variety.

The photographs were taken using conventional techniques and although colors may appear different from actual colors due to light reflectance it is as accurate as possible by conventional photographic techniques.

EXAMPLES

Botanical Description

In the following description, color references are made to the Royal Horticultural Society Mini Colour Chart 2005 except where general terms of ordinary dictionary significance are used. The following observations and measurements describe 'DAPORUMDBL' plants grown outdoors in Nir Zvi, Israel, under natural lighting. Measurements were taken during Spring. The growing temperature ranged from approximately 27° C. to 35° C. during the days, 16° C. to 20° C. during the nights. Measurements and numerical values represent averages of typical plant types.

Botanical classification: *Portulaca umbraticola* 'DAPORUMDBL'

Propagation

Time to Initiate Rooting: Vegetative cuttings
Root Description: 10 to 14 days at approximately 20° C.

Root Description: Fine, fibrous; close to Yellow-White 158D in color, freely branching.

Plant

Growth Habit: Semi-trailing
Age of Plant Described: Approximately 10 weeks from a rooted cutting.
Pot size of plant described: 13 cm.
Height: About 22 cm.
Plant Spread: About 24 cm radius.
Growth Rate: Medium vigor.
Branching Characteristics:
Length of Primary Lateral Branches: 27 cm.
Diameter of Lateral Branches: 0.6 cm.
Quantity of Primary Lateral Branches: About 10 per 1 main stem
Characteristics of Primary Lateral Branches:
   Diameter: About 0.35 to 0.4 cm
   Color: Tip Near Yellow-Green RHS 144B; Base near RHS Red-Purple 59C(Anthocyanin coloration)
   Texture: Glabrous.
   Strength: Moderately strong.
Internode length: Approximately 1.8 to 3.0 cm.

Foliage

Leaf:
   Arrangement. Alternate, simple
   Quantity: Approximately 16 per branch.
   Average Length: 2.7 cm.
   Average Width: 1.5 to 2.0 cm.
   Shape of blade: Obovate.
   Apex: Obtuse. Young foliage broad acute.
   Base: Cuneate.
   Margin: Entire
   Texture of top surface: Smooth
   Texture of bottom surface: Smooth
   Pubescence: None.
   Aspect: Straight, occurring at an able of about 45°-75°
Color:
   Young foliage upper side: Near RHS 137B
   Young foliage under side: Near RHS Yellow-Green 147B
   Mature foliage upper side: Near RHS Yellow-Green 147A
   Mature foliage under side: Near RHS Yellow-Green 147B
Venation: Indistinguishable from leaf blade.
Petiole:
Length: About 1.5 mm
Diameter. About 1.2 mm
Color: Near RHS Yellow-Green 144A
Texture: Smooth, glabrous Flower Bloom Period:
   Natural Season: Spring to Fall.
Days to flowering from rooted cutting: About 4 to 6 weeks to the first flowers.
Inflorescence and flower type and habit: Semi-double flower, abundant flowering.
Rate of flower opening: About 4 to 6 days from bud to fully opened flower.
Flower Longevity on Plant: About 1 days.
Persistent or Self-Cleaning: Self-Cleaning
Bud:
   Shape: Ovoid
   Length: 1 to 1.2 cm
   Diameter: 0.6 cm
   Color: Near RHS Yellow-Green 144A.
Flower size:
   Diameter: About 3.4 cm.
   Depth: About 2.4 cm.
Corolla/Petals:
   Arrangement: 5 petals merged/fused at the base. 3 to 9 center petals(number varies according to environmental conditions. When plants are given shade, less center petals are observed.
   Length: Outer petals about 1.9 cm Center petals about 1.6 cm.
   Width: Outer petals about 1.6 cm Center petals about 0.6 cm to 1.0 cm.
   Texture: Smooth, glabrous
   Apex: Outer petal retuse. Center petals mucronate.
   Shape: Obovate with a cuneate base
   Margin: Entire
   Color: When opening:
   Upper surface: RHS Red-Purple 72D
   Lower surface: RHS Red-Purple 73A
   Fully opened:
   Upper surface: RHS Red-Purple 73A
   Lower surface: RHS Red-Purple 73B
Calyx/Sepals:
   Quantity per flower: 2 Sepals per flower.
   Shape: fused into a tubular calyx. Pointed apex.
   Length: 0.7 cm
   Width: 0.5 cm
   Apex: Acute
   Base: Fused
   Margin: Entire
   Texture: Glabrous
   Color: Upper Surface: Near RHS Green 143A.
   Lower Surface: Near RHS Green 143C.
Peduncle: None
Fragrance: None detected.

Reproductive Organs

Androecium
Stamens:
   Number: Many, about 50.
   Filament length: Approximately 0.4 cm to 0.6 cm.
Anthers:
   Shape: Oval
   Length: About 0.5 mm
   Color: Near RHS Yellow-Orange 15A
Pollen:
   Color: RHS Yellow-Orange 17B
   Quantity: Scant
Gynoecium
Pistil:
   Number: 1
   Length: 0.9 cm.
Style:
   Length: 0.8 cm.
   Color: Base near RHS Yellow 8C.
Stigma:
   Shape: 4 to 5 branched stigma
   Color: Near RHS Yellow 8B.
Ovary Color: Near RHS Yellow-Green 144B Other Characteristics Seeds and fruits: Seeds are minute and dark grey with a circular shape.

Disease/pest resistance: Neither resistance nor susceptibility observed. *Portulaca* is not typically susceptible to many diseases and pests. The most common diseases being typical root rots from over watering, or black stem, *Dichotomophthora portulaca*. The most common pest of *Portulaca* is Aphid.

Temperature tolerance: Will not tolerate temperatures below 7° C. High temperature tolerance near 40° C.

We claim:

1. A plant of *Portulaca* variety named 'DAPORUMDBL', representative biological material seed deposited and accepted under the Budapest Treaty at the NCIMB in Aberdeen, Scotland and assigned accession number NCIMB 43738.

2. A plant part of the plant of claim 1, wherein the plant part comprises at least one cell of *Portulaca* 'DAPORUMDBL'.

3. A *Portulaca* plant, having all the physiological and morphological characteristics of the plant of variety named 'DAPORUMDBL' of claim 1.

4. A tissue or cell culture of regenerable cells produced from the plant of claim 1.

5. The tissue or cell culture of claim 4, comprising tissues or cells from a plant part selected from the group consisting of leaves, vegetative cuttings, pollen, embryos, cotyledons, hypocotyl, meristematic cells, roots, root tips, pistils, anthers, flowers and stems.

6. A method of producing *Portulaca* progeny comprising the steps of (a) crossing a plant of *Portulaca* 'DAPORUMDBL' as a female or male parent with another *Portulaca* plant and (b) selecting progeny.

7. The method according to claim 6, wherein the second plant is *Portulaca* 'DAPORUMDBL'.

8. A *Portulaca* seed that produces the *Portulaca* plant of claim 1.

9. A method for developing a *Portulaca* plant in a plant breeding program using plant breeding techniques, including crossing, recurrent selection, mutation breeding, wherein said mutation breeding selects for a mutation that is spontaneously or naturally induced or artificially induced, backcrossing, pedigree breeding, marker enhanced selection, haploid/double haploid production or transformation to a plant of *Portulaca* 'DAPORUMDBL', or it's its parts, or an F1 progeny wherein application of said techniques results in development of a *Portulaca* plant.

* * * * *